United States Patent [19]

Harris et al.

[11] Patent Number: 5,578,446
[45] Date of Patent: Nov. 26, 1996

[54] ANALYTICAL DIPSTICK FOR IMPROVED MIXING AND REDUCED REAGENT VOLUME

[75] Inventors: Paul C. Harris, Edmonds; Jack R. U'Ren, Kirkland, both of Wash.

[73] Assignee: Becton Dickinson and Company, Franklin Lakes, N.J.

[21] Appl. No.: 272,202

[22] Filed: Jul. 8, 1994

[51] Int. Cl.$^6$ .................................................. C12Q 1/68
[52] U.S. Cl. ............... 435/6; 435/4; 435/5; 435/7.1; 435/7.5; 435/7.92; 435/970; 435/973; 435/975; 436/518; 436/524; 436/525; 436/528; 436/530; 436/531; 436/808; 436/809; 436/810; 422/58
[58] Field of Search ........................ 422/58; 435/4, 435/5, 6, 7.1, 7.5, 7.92, 970, 973, 975; 436/518, 524, 525, 528, 530, 531, 808–810

[56] References Cited

U.S. PATENT DOCUMENTS

| | | | |
|---|---|---|---|
| 4,135,884 | 1/1979 | Shen | 422/58 X |
| 4,146,365 | 3/1979 | Kay et al. | 422/58 X |
| 4,200,613 | 4/1980 | Alfrey et al. | 436/809 X |
| 4,205,043 | 5/1980 | Esch et al. | 422/58 X |
| 4,225,575 | 9/1980 | Piaso et al. | 422/58 X |
| 4,299,916 | 11/1981 | Litman et al. | 435/7.92 |
| 4,495,151 | 1/1985 | Ohyama et al. | 435/7.9 |
| 4,822,565 | 4/1989 | Kohler | 436/518 X |
| 5,017,342 | 5/1991 | Haberzettl et al. | 436/810 X |
| 5,126,276 | 6/1992 | Fish et al. | 436/531 X |

Primary Examiner—Carol A. Spiegel
Attorney, Agent, or Firm—Townsend and Townsend and Crew

[57] ABSTRACT

The analytical dipstick of the present invention facilitates analyte testing with reduced liquid reagent volumes and provides improved mixing. The dipstick includes an elongated member having a fluid displacing member at one end thereof and a ligand attached to a portion of the elongated member in a region adjacent to the displacing member. The displacing member has a configuration that substantially conforms with the inner side wall of an analytical well in which the dipstick is placed to displace fluid therein. When the displacing member is substantially centered at the bottom of the well, the portion of the dipstick supporting the ligand preferably is spaced from the inner side wall by a distance of at least about twice that between the displacing member and the inner side wall, measured along a line passing through the greatest lateral dimension of the displacing member. With this configuration, essentially all of the liquid at the bottom of the well is displaced upwardly so that the ligand is immersed therein. The relatively large space between the intermediate portion and the side wall of the well facilitates turbulent flow to enhance mixing in the region of the ligand.

23 Claims, 1 Drawing Sheet

ANALYTICAL DIPSTICK FOR IMPROVED MIXING AND REDUCED REAGENT VOLUME

FIELD OF THE INVENTION

This invention generally relates to a dipstick for detection of analytes. More particularly, this invention relates to a dipstick configuration which minimizes the required reagent volume and produces more even mixing when reciprocated in and out of an analytical well.

BACKGROUND OF THE INVENTION

The use of "dipsticks" in assaying for the presence of an analyte in a sample is known in the art. Typical analytes comprise such materials as drugs, nucleic acids, proteins, pollutants, fine chemicals, such as, physiological compounds, and the like. In a typical dipstick based analytical assay, a ligand, which specifically binds to the analyte of interest, is bound to a solid support on the dipstick. The dipstick is contacted with a sample in which the presence of the analyte of interest is to be determined. Frequently, steps are employed to aid in the removal of non-specifically bound material from the dipstick. Finally, the dipstick is processed to determine the presence of the analyte. The dipstick generally comprises a solid material, which is planar or columnar in geometry. U.S. Pat. No. 4,391,904 to Litman et al. (incorporated herein by reference) describes test strip kits wherein a member of an immunological pair is bonded to a solid surface. Herzberg et al., U.S. Pat. No. Des. 293,374, disclose an assay card with tapered ends.

In one widespread format, the dipstick is transferred through one or more liquid reagent filled analytical wells. In this format, complete immersion of the solid support requires filling the analytical well with liquid reagent to a depth which approximates the distance between the solid support and the distal end of the dipstick. While this format provides a convenient means of assaying for an analyte, the cost of the liquid reagent may dramatically increase the cost of the assay and increasing the volume of the reagent by dilution decreases the inherent sensitivity of the assay. Mixing of the liquid by reciprocating the dipstick in and out of the solution is frequently used to hasten processing. However, the configuration of prior art dipsticks is not optimized to perform this function. Further, upon removal from the reagent, droplets suspended from the dipstick may contaminate subsequent processing steps necessitating longer or additional processing.

In developing an assay, it is desirable to minimize the number of processing steps, the time between steps, and the reagent volume employed at each step, while simultaneously maximizing the sensitivity of the assay. While effort has been made to optimize reagent chemistry to achieve these ends, the analytical dipstick configuration has changed little. It is therefore desirable to develop a novel dipstick configuration for improving assay performance.

SUMMARY OF THE INVENTION

The present invention is directed to an analytical dipstick that avoids the problems and disadvantages of the prior art. According to the present invention, which has particular utility in assays requiring processing in a liquid reagent, an analytical dipstick comprising an elongated member having a first end portion, a second end portion and an intermediate portion positioned between said first and second end portions is provided. The thickness of the elongated member, measured in one direction, substantially increases from the intermediate portion to the second end portion. A ligand, which is selected to be specific to the analyte of interest, is coupled to the intermediate portion in a region adjacent to the second end portion of the elongated member.

In operation, the dipstick is inserted into a well containing a liquid (e.g., a reagent containing an analyte). The enlarged second end portion of the dipstick is configured so that when it is substantially centered at the base or bottom of the well, it displaces essentially all of the liquid at the bottom of the well through a small space or passage formed between the second end portion and the side wall of the well. The displaced liquid then rises along the intermediate portion so that the ligand becomes immersed in the liquid.

Since the enlarged second end portion can displace essentially all of the liquid at the bottom of the well upwardly to immerse the ligand therein, analyte testing can be conducted with minimal amounts of reagent with the present invention. That is, the second end portion can be configured so that the distance between the terminus of the second end portion and the ligand can be greater than the depth of liquid in the analytical well, thereby permitting analyte testing with reduced reagent volumes.

In the preferred embodiment, the second end portion is configured so that it essentially fills the space at the base of the well, thereby displacing essentially all of the liquid at the base of the well upward. When the second end portion is centered at the base of the well, the space between the second end portion and the inner side wall of the well, measured along a line extending through the maximum lateral dimension of the second end portion, preferably is to about 0.005 to 0.030 inches, and more preferably about 0.010 to 0.020 inches. This configuration provides virtually complete displacement of the liquid at the base of the well, while permitting the development of desirable laminar flow adjacent to the second end portion.

Another important aspect of the invention is that the portions of the outer surface of the intermediate portion that are closest to the center axis of the intermediate portion are spaced from the inner side wall of the well by an amount substantially greater than that between the second end portion and the inner side wall of the well, measured along a line extending through the maximum lateral dimension of the second end portion. More specifically, the locus of points on the outer surface of the intermediate portion, which are closest to the center axis of the intermediate portion, are spaced from the inner side wall by a distance at least twice that between the second end portion and the inner side wall of the well, measured along a line extending through the maximum lateral dimension of the second portion. When the second end portion of the dipstick is forced downward toward the closed end or base of the well, the reagent or liquid at the closed end is forced upward toward the intermediate portion. The space between the second end portion and the side wall of the well facilitates laminar flow therebetween. However, upon entering the enlarged space between the inner side wall of the well and the intermediate portion, the laminar flow of the fluid is disrupted resulting in eddy currents. The eddy currents advantageously improve mixing in that region which hastens transfer of reactant into or out of the microscopic zone surrounding the ligand, thereby improving reaction kinetics. Repetition of this procedure, by reciprocating the dipstick in and out of the liquid reagent, continuously disrupts the microscopic zone and reduces processing time and/or increases sensitivity.

The terminal end surface of the second end portion preferably has a curved surface or a projection, which can be in the form of a spike, to minimize surface tension between the liquid in the well and the second end portion when removing that portion from the liquid. This construction provides a relatively small interface between the second end portion and the liquid as the second end portion is removed therefrom which reduces the size of any drop that adheres to the second end portion upon removal from the liquid reagent. The rounded terminal end surface of a spherically, hemispherically or teardrop shaped second end portion provides the desired results, for example. However, when the terminal end surface of the second end portion is flat, a projection is provided to extend from that surface to reduce the size of any drop hanging from the terminal end surface when the second end portion is removed from the liquid.

In the preferred embodiment, the ligand is attached to a solid support which is a discrete component which, in turn, is attached to the intermediate portion of the dipstick.

Preferably, the face of the first end portion and intermediate portion is planar in configuration and the solid support is a bead which is inserted into a perforation in the face by means of a pressure fit. Alternatively, the solid support is formed as an integral part of the intermediate portion.

The above is a brief description of some deficiencies in the prior art and advantages of the present invention. Other features, advantages and embodiments of the invention will be apparent to those skilled in the art from the following description, accompanying drawings and appended claims.

DESCRIPTION OF THE PREFERRED EMBODIMENT

Figure 2:
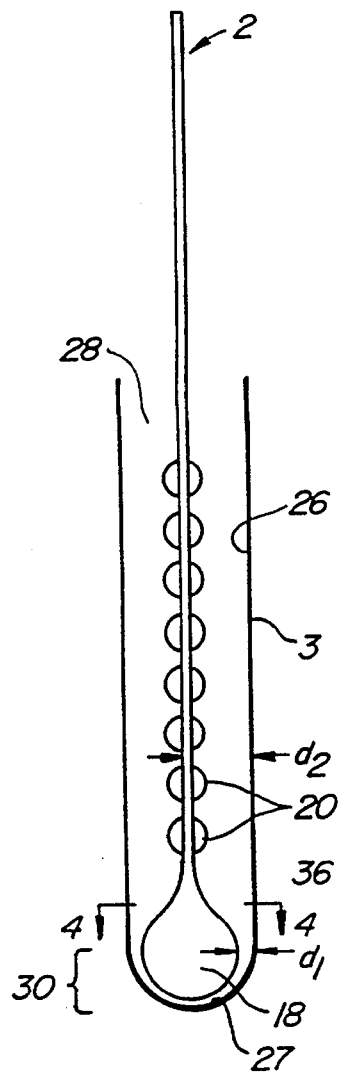
FIG. 2 shows the a dipstick of FIG. 1 rotated 90° and positioned in an analytical well.

Referring to the drawings in detail wherein like numerals indicate like elements, an apparatus 1 for testing for the presence of analytes, for example, is shown in accordance with the principles of the present invention. Referring to FIG. 2, apparatus 1 generally comprises an analytical dipstick 2, which facilitates testing with reduced liquid reagent volumes and improves mixing, and fluid holding container 3.

Figure 1:
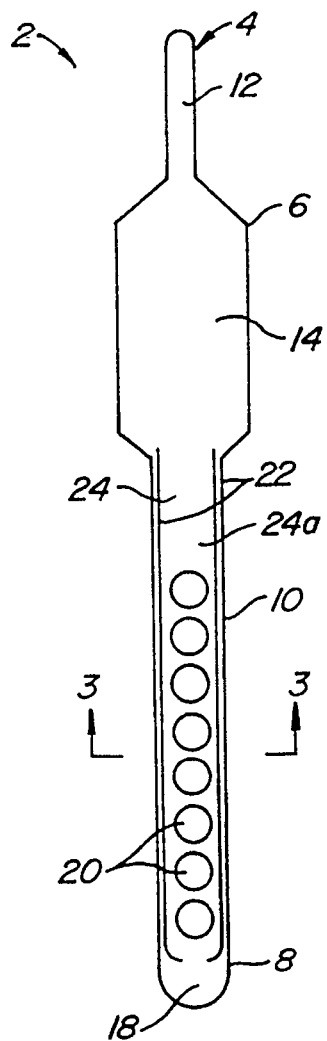
FIG. 1 is a front view of a dipstick constructed according to the principles of the present invention.

Referring to FIG. 1, dipstick 2 generally comprises an elongated member 4 which includes a first or proximal end portion 6, a second or distal end portion 8 and an intermediate or carrier portion 10 therebetween. First end portion 6 includes a gripping member or section 12 and a generally planar section 14 which can serve as a display surface for a label. Second end portion 8 forms a fluid displacing member 18 which will be described in more detail below. Intermediate portion or carrier 10 carries one or more ligands. In the illustrated embodiment, solid supports 20, which are coated covalently or non-covalently with a ligand, are coupled to the carrier. The composition of the elongated member and solid support may be selected from a variety of materials such as nitrocellulose, plastic, ceramic, metal, polymers or combinations thereof.

The term "ligand" as used herein refers to a variety of different binding agents and molecules that are bound by binding agents. Ligands are useful in a variety of different in vitro assays, such as immunoassays, receptor binding assays, and nucleic acid hybridization assays and the like. Ligands can be coupled to solid supports which can be used in a variety of different solid phase assay formats.

A variety of different solid phase assay formats are well known in the art. For example, immunoassay formats are described in *Basic and Clinical Immunology* 7th Edition (D. Stites and A. Terr ed.) 1991. Immunoassays can be performed in many configurations, examples of which are reviewed in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B. V. Amsterdam (1985); and, Harlow and Lane, *Antibodies, A Laboratory Manual*, supra, each of which is incorporated herein by reference. A variety of nucleic acid hybridization formats are also known to those skilled in the art. For example, common formats include sandwich assays and competition or displacement assays. Hybridization techniques and formats are generally described in *"Nucleic Acid Hybridization, A Practical Approach,"* Ed. Hames, B. D. and Higgins, S. J., IRL Press, 1985; Gall and Pardue (1969), *Proc. Natl. Acad. Sci.*, U.S.A., 63:378–383; and John, Burnsteil and Jones (1969) *Nature*, 223:582–587.

In the preferred embodiment, each solid supports 20 comprises a bead-like member, which can be spherical, for example. The bead-like member has an outer surface that is appropriate for attachment to a ligand. A variety of ligands can be attached to a variety of different solid supports as disclosed in Litman et al., U.S. Pat. No. 4,391,904 which is hereby incorporated herein by reference.

A ligand, which specifically binds to the analyte whose presence is assayed for, is attached to the coating. A variety of different ligands can be used to detect many analytes of scientific, medical and industrial interest. Such ligands include, but are not limited to, nucleic acids, antibodies, proteins, enzymes, receptors, hormones, streptavidin and biotin.

Figure 3:
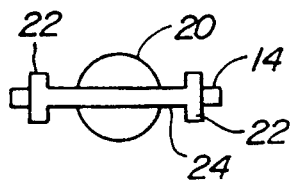
FIG. 3 is a section of the dipstick taken along line 3—3 in FIG. 1.

Returning to FIGS. 1 and 2, more than one solid support can be bound to carrier 10 with each solid support coated with identical, different, or combinations of ligands. The surface area of carrier 10 generally should be minimized to avoid non-specific binding of material which may interfere with subsequent processing of the dipstick and, thus, should generally be smooth in texture and planar in configuration. The cross-sectional thickness of carrier 10 should be sufficient to maintain rigidity of the dipstick as it is reciprocated in and out of a liquid reagent contained in container 3. In the preferred embodiment, carrier 10 has an I-beam configuration to add rigidity to the carrier. As shown in FIGS. 1 and 3, carrier 10 can comprise flange 22 and web 24, with flanges 22 being constructed so as to be generally parallel to inner side wall 26 of container 3 when elongated member 4 is disposed in recess 28 of the container as shown in FIG. 2.

In the preferred embodiment, solid support(s) 20 is a discrete component which is coupled to carrier 10. Preferably, web 24 includes one or more openings which can be a depression or perforation (through-hole), to hold one or more solid supports 20. The solid support can be roughened by chemical or physical means prior to coating with the ligand to maximize the reactive surface area via microscopic indentations and channels. In the preferred embodiment, the solid support comprises a roughened spherical bead which is inserted into a perforation in carrier 10 as shown in FIGS. 1 and 2 and held in place by means of a pressure fit. A pressure fit can be achieved by providing a perforation having a diameter only slightly smaller than that of the bead as would be readily apparent to one of ordinary skill. Although a particular ligand attachment arrangement has been described, other arrangements can be used. For example, the solid support can simply be a part of or integrated with the carrier and the ligand can be attached directly to the solid support. See, e.g., Litman et al., U.S. Pat. No. 4,391,904 which is hereby incorporated herein by reference.

Figure 4:
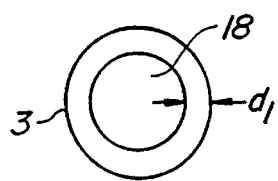
FIG. 4 is a section of the dipstick and well apparatus taken along line 4—4 in FIG. 2.

Displacing member 18 acts to displace liquid reagent in container 3 up from the closed end of the container to immerse the solid support in the liquid reagent. The carrier preferably is positioned close to the displacing member, relative to the length of the dipstick, to aid in minimizing the amount of reagent volume needed to perform a test. Displacing member 18 has a configuration and is of sufficient volume to essentially fill recess 28 at the base of container 3 so that it displaces essentially all of the liquid reagent at the bottom or base 30 of container 3. Accordingly, the configuration of the outer surface of the lower portion of member 18 substantially conforms with the configuration of inner side wall 26 and the inner bottom wall 27 at the bottom region of recess 28. Thus, when displacing member 18 is hemispherical, it has a cross-section, taken as a plane along the center axis of recess 28, which is in substantial conformity with the inner side wall 26 at the bottom region 30 of recess 28. Preferably, the displacing member 18 is configured so that the distance $d_1$ between the displacing member and inner side wall 26, measured along a line through the maximum lateral dimension of the displacing member (as shown in FIG. 2) is about 0.005 to 0.030 inches, and most preferably, 0.010 to 0.020 inches. See also FIG. 4.

Figure 5:
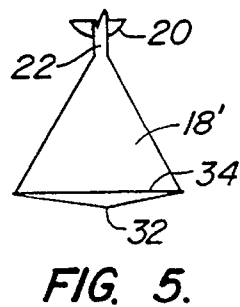
FIG. 5 shows a further embodiment of the dipstick displacing member according to the present invention.

The average distance between either the front web face 24a and inner side wall 26 or the rear face (which is hidden from view) of web 24 and inner side wall 26 preferably is substantially greater than $d_1$ to facilitate turbulent flow in the solid support region of carrier 10. Preferably, the distance $d_2$ between a web face and side wall 26, measured along a line passing through the center axis of carrier 10 and being essentially perpendicular to the respective web face is at least about twice $d_1$ when the displacing member is centered at the bottom of recess 28. Preferably, voids such as depressions or perforations within the displacing member, which would trap liquid upon insertion of the displacing means into the liquid, are absent. In addition, the displacing member is generally configured such that its terminal end surface, which directly opposes the closed end of the well, has a minimal surface area. A minimal surface area reduces the size of any drop hanging from or adhering to the displacing member when the dipstick is removed from the liquid in container 3. This results in less carryover to subsequent containers or wells. Accordingly, the distal end surface of member 18 preferably is either pointed or curved. Preferred displacing member configurations having a minimal distal area are spherical, hemispherical, or teardrop configurations. When a triangular solid (tetrahedron) configuration is used for the displacing member, as shown with displacing member 18' in FIG. 5, a projection 32, which can be in the form of a tetrahedron or pyramid, for example, preferably is provided on the bottom surface 34 of member 18' to eliminate the otherwise flat surface and, thus, reduce the size of any hanging drop. Similarly, if a conical shape is used for the displacing member, its bottom surface can be configured to end in a point. The transition from carrier 10 to the displacing member preferably is gradual, preferably by way of a curve (as illustrated in FIG. 2 and generally designated with reference numeral 36) or positively angled line so as to avoid level areas or voids which could trap liquid.

The container used in conjunction with the dipstick may be in a variety of sizes and cross-sectional shapes such as square, round, or rectangular and therefore includes tubes and microtiter wells. The shape of the cross-section of the closed end of the recess will be of the same shape as a cross-section of the base region of the displacing member, disregarding minor indentations or voids within the displacing member. In the preferred embodiment, the container recess or well is circular in transverse section with a rounded bottom and the displacing member is hemispherical to conform with the shape of the well and displace a maximum amount of fluid.

The present invention provides the advantages of lower reagent volume and improved mixing when vertically reciprocated in and out of a liquid reagent in a container 3. The displacing member should be immersed sufficiently deep into the liquid, and sufficient liquid used, such that the displacing member displaces the liquid upward and causes immersion of the solid support. The relatively large space between the side wall and the web faces disrupts the laminar flow exiting from the passage formed between the displacing member and side wall 26. This produces swirling eddy currents which results in enhanced mixing which is particularly important when mixing liquid reagents comprising a colloidal suspension. Since the reaction kinetics are limited by the rate of diffusion into and out from the a microscopic zone surrounding the solid support, more mixing steepens the concentration gradient extending from the solid support and narrows the reactant zone surrounding the solid support. Reduction of the reactant depletion zone hastens processing time and/or increases sensitivity. Withdrawal of the dipstick to allow the reagent to pool at the closed end of the recess permits repetition of the cycle.

The above is a detailed description of a particular embodiment of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

What is claimed is:

1. An analytical dipstick comprising:

an elongated member having a first end portion, a second end portion and an intermediate portion positioned between said first and second end portions, the thickness of said elongated member, measured in one direction, substantially increasing from a location on said intermediate portion to said second end portion, said second end portion having a thickness, measured along a line passing through a maximum lateral dimension of said second end portion, at least twice that of a thickness, measured along said one direction, of said intermediate portion at said location; and a ligand coupled to said intermediate portion between said location on said intermediate portion and said first end portion.

2. The dipstick of claim 1 wherein said elongated member is rigid.

3. The apparatus of claim 2 wherein said intermediate portion has an I-beam configuration.

4. The dipstick of claim 1 wherein the change in said thickness between said location on said intermediate portion and second end portion is gradual.

5. The dipstick of claim 1 wherein said intermediate portion is planar.

6. The dipstick of claim 1 wherein said first end portion is planar and includes a surface for receiving identification information.

7. The dipstick of claim 1 wherein said second end portion has a hemispherically shaped end surface.

8. The dipstick of claim 1 wherein said second end portion has one of a conical and tetrahedral configuration with a pointed bottom end surface.

9. The dipstick of claim 1 wherein said ligand is selected from the group consisting of an antibody, enzyme, nucleic acid, streptavidin and a biotin.

10. The dipstick of claim 1 wherein said ligand is a protein.

11. An analyte testing apparatus comprising:
a container having a recess formed therein, said recess being defined by at least one side wall and a bottom wall; and
an elongated member slidably receivable in said recess, said elongated member having a first end portion, a second end portion that forms a displacing member and an intermediate portion positioned between said first and second end portions, said intermediate portion having a ligand coupled thereto in a region adjacent to said displacing member, said displacing member essentially filling the portion of said recess that is adjacent to said bottom wall when said displacing-member is positioned thereagainst, said intermediate portion including an outer surface having first and second regions, said first region being closer to a center axis of said intermediate portion than said second region, the distance between any point in said first region and said at least one side wall being at least about twice the distance between said displacing member and said side wall, measured along a line passing through the maximum lateral dimension of said displacing member, when said displacing member is centered at a bottom portion of said recess.

12. The apparatus of claim 11 wherein the configuration of said displacing member substantially conforms to the configuration of the corresponding boundary of said container recess adjacent to said bottom wall.

13. The apparatus of claim 11 wherein the distance between said displacing member and said at least one inner side wall, measured along a line through the maximum lateral dimension of the second end portion, is about 0.005 to 0.030 inches when said displacing member is centered at the bottom of said recess.

14. The apparatus of claim 13 wherein said intermediate portion includes an outer surface area that is spaced from said at least one side wall by a distance that is substantially greater than said distance between said displacing member and said at least one side wall.

15. The apparatus of claim 11 wherein said displacing member is teardrop shaped.

16. The apparatus of claim 11 wherein said displacing member is spherical.

17. The apparatus of claim 11 wherein said displacing member is hemispherical.

18. The apparatus of claim 11 wherein said displacing member is configured in the form of a tetrahedron.

19. The apparatus of claim 11 further including a solid support in the form of a bead, said intermediate portion including an opening, said ligand being attached to said solid support and said solid support being positioned in said opening.

20. The apparatus of claim 11 wherein said ligand is selected from the group consisting of an antibody, enzyme, nucleic acid, streptavidin and biotin.

21. The apparatus of claim 11 wherein the configuration of a transverse section of said recess adjacent said bottom wall is selected from the group consisting of square, rectangular and circular.

22. The apparatus of claim 21 wherein the configuration of a transverse section of said displacing member is essentially identical to the configuration of said transverse section of said recess.

23. The apparatus of claim 11 wherein said ligand is a protein.

* * * * *